(12) United States Patent
Johnson

(10) Patent No.: US 9,881,024 B1
(45) Date of Patent: Jan. 30, 2018

(54) MOBILE HEALTHCARE APPLICATION FOR FACILITATING COLOR DETERMINATION

(71) Applicant: ALLSCRIPTS SOFTWARE, LLC, Chicago, IL (US)

(72) Inventor: Mary Sumner Johnson, Raleigh, NC (US)

(73) Assignee: ALLSCRIPTS SOFTWARE, LLC, Chicago, IL (US)

( * ) Notice: Subject to any disclaimer, the term of this patent is extended or adjusted under 35 U.S.C. 154(b) by 454 days.

(21) Appl. No.: 14/528,349

(22) Filed: Oct. 30, 2014

(51) Int. Cl.
| | |
|---|---|
| H04N 7/18 | (2006.01) |
| G06F 17/30 | (2006.01) |
| G06F 19/00 | (2011.01) |
| H04N 5/232 | (2006.01) |
| G06T 7/40 | (2017.01) |
| G06T 7/00 | (2017.01) |
| A61B 5/00 | (2006.01) |

(52) U.S. Cl.
CPC .......... *G06F 17/3025* (2013.01); *A61B 5/742* (2013.01); *G06F 19/321* (2013.01); *G06T 7/0014* (2013.01); *G06T 7/408* (2013.01); *H04N 5/23293* (2013.01); *G06T 2207/10024* (2013.01); *G06T 2207/30088* (2013.01)

(58) Field of Classification Search
CPC .......... G06F 17/3025; G06F 17/30244; G06F 17/30247; G06F 19/321; A61B 5/742; G06T 7/0014; G06T 7/408; H04N 5/23293

See application file for complete search history.

(56) References Cited

U.S. PATENT DOCUMENTS

| | | | | |
|---|---|---|---|---|
| 2005/0288568 | A1* | 12/2005 | Pan ...................... | G06F 19/321 600/407 |
| 2012/0106811 | A1* | 5/2012 | Chen ..................... | G06T 7/0012 382/128 |
| 2012/0200850 | A1* | 8/2012 | Stewart .................. | G01N 21/65 356/301 |
| 2014/0275948 | A1* | 9/2014 | Kamisoyama ....... | A61B 5/6898 600/407 |
| 2016/0073908 | A1* | 3/2016 | Khachaturian .......... | A61B 5/01 600/474 |

* cited by examiner

*Primary Examiner* — Tat Chio
(74) *Attorney, Agent, or Firm* — Tillman Wright, PLLC; Chad D. Tillman; Jeremy C. Doerre

(57) ABSTRACT

A method for assisting a health care practitioner in color evaluation includes maintaining, in a database, a plurality of images each corresponding to a particular result or condition; capturing, by a healthcare practitioner using a camera of a mobile electronic device, a subject image of a patient or an object associated with the patient; automatically comparing, utilizing one or more electronic processors, the captured subject image to images maintained in the database, such comparison including comparing one or more colors in the subject image to one or more colors in the images maintained in the database; automatically determining, based on the automatic comparison, that the captured subject image is positively matched to one or more of the plurality of images maintained in the database; and displaying an indication of the particular result or condition corresponding to each of the positively matched plurality of images.

16 Claims, 4 Drawing Sheets

MOBILE HEALTHCARE APPLICATION FOR FACILITATING COLOR DETERMINATION

COPYRIGHT STATEMENT

All of the material in this patent document is subject to copyright protection under the copyright laws of the United States and other countries. The copyright owner has no objection to the facsimile reproduction by anyone of the patent document or the patent disclosure, as it appears in official governmental records but, otherwise, all other copyright rights whatsoever are reserved.

BACKGROUND OF THE INVENTION

The present invention generally relates to color determination.

Both color deficiencies in vision and environmental variances affect how people perceive color differences. It has been estimated that humans can distinguish roughly 10 million different colors but the identification of a specific color is highly subjective. Even users with normal vision can perceive colors slightly different from eye to eye. Color perception changes with aging, light source (fluorescent, LED, halogen, natural light, etc.), and surrounding color reflections. Even a person's emotional state can have an effect on color perception.

Further, vision deficiencies related to color identification exist in a large number of individuals: approximately one in twelve men and one in one hundred women.

In a healthcare context, an inability to identify or discriminate colors could potentially compromise patient safety. Despite this, however, only a small portion of practicing healthcare providers have been tested for color deficiencies, and many individuals are unaware of their deficiency.

A need exists for improvement in color discrimination. This need, and other needs, are addressed by one or more aspects of the present invention.

SUMMARY OF THE INVENTION

The present invention includes many aspects and features. Moreover, while many aspects and features relate to, and are described in, a particular context, the present invention is not limited to use only in such context, as will become apparent from the following summaries and detailed descriptions of aspects, features, and one or more embodiments of the present invention.

Accordingly, one aspect of the present invention relates to a method for assisting a health care practitioner in color evaluation, the method comprising maintaining, in a database, a plurality of images each corresponding to a particular result or condition; capturing, by a healthcare practitioner using a camera of a mobile electronic device, a subject image of a patient or an object associated with the patient; automatically comparing, utilizing one or more electronic processors, the captured subject image to images maintained in the database, such comparison including comparing one or more colors in the subject image to one or more colors in the images maintained in the database; automatically determining, based on the automatic comparison, that the captured subject image is positively matched to one or more of the plurality of images maintained in the database; and displaying, to the healthcare practitioner via a display of the mobile electronic device, an indication of the particular result or condition corresponding to each of the positively matched plurality of images.

In a feature of this aspect, the mobile electronic device comprises a phone.

In a feature of this aspect, the mobile electronic device comprises a touchscreen.

In a feature of this aspect, the mobile electronic device comprises a tablet.

In a feature of this aspect, the database comprises a database stored at the mobile electronic device.

In a feature of this aspect, the database comprises a remote database.

In a feature of this aspect, the automatic comparison occurs at a remote server.

In a feature of this aspect, the automatic comparison occurs at the mobile electronic device.

Another aspect relates to a method for assisting a health care practitioner in color evaluation, the method comprising maintaining, in a database, a plurality of images of various body parts and objects, each image corresponding to a particular result or condition; receiving, at a mobile electronic device, input from a healthcare practitioner corresponding to an identification of a particular body part or object for which an image is to be captured; capturing, by the healthcare practitioner using a camera of the mobile electronic device, a subject image of a body part of a patient or an object associated with the patient; determining a subset of the maintained plurality of images which correspond to the identified particular body part or object; automatically comparing, utilizing one or more electronic processors, the captured subject image to the subset of images maintained in the database which are associated with the identified particular body part or object, such comparison including comparing one or more colors in the subject image to one or more colors in the subset of images; automatically determining, based on the automatic comparison, that the captured subject image is positively matched to one or more of the plurality of images maintained in the database; and displaying, to the healthcare practitioner via a display of the mobile electronic device, an indication of the particular result or condition corresponding to each of the positively matched plurality of images.

In a feature of this aspect, the mobile electronic device comprises a phone.

In a feature of this aspect, the mobile electronic device comprises a touchscreen.

In a feature of this aspect, the database comprises a database stored at the mobile electronic device.

In a feature of this aspect, the database comprises a remote database.

In a feature of this aspect, the automatic comparison occurs at a remote server.

In a feature of this aspect, the automatic comparison occurs at the mobile electronic device.

In a feature of this aspect, the identification of a particular body part or object comprises identification of a test strip.

In a feature of this aspect, the identification of a particular body part or object comprises identification of a urine sample.

In a feature of this aspect, the identification of a particular body part or object comprises identification of a patient's skin.

In a feature of this aspect, the identification of a particular body part or object comprises identification of a patient's eye.

Another aspect relates to a method for assisting a health care practitioner in color evaluation, the method comprising maintaining, in a database, a plurality of images each corresponding to a particular result or condition; capturing, by a healthcare practitioner using a camera of a mobile electronic device, a subject image of a patient or an object associated with the patient; automatically comparing, utilizing one or more electronic processors, the captured subject image to images maintained in the database, such comparison including comparing colors of one or more pixels in the subject image to colors of one or more pixels in the images maintained in the database; automatically determining, based on the automatic comparison, that the captured subject image is positively matched to one or more of the plurality of images maintained in the database; and displaying, to the healthcare practitioner via a display of the mobile electronic device, an indication of the particular result or condition corresponding to each of the positively matched plurality of images.

In addition to the aforementioned aspects and features of the present invention, it should be noted that the present invention further encompasses the various possible combinations and subcombinations of such aspects and features. Thus, for example, any aspect may be combined with an aforementioned feature in accordance with the present invention without requiring any other aspect or feature.

BRIEF DESCRIPTION OF THE DRAWINGS

One or more preferred embodiments of the present invention now will be described in detail with reference to the accompanying drawings, wherein the same elements are referred to with the same reference numerals, and wherein.

DETAILED DESCRIPTION

Figure 1:
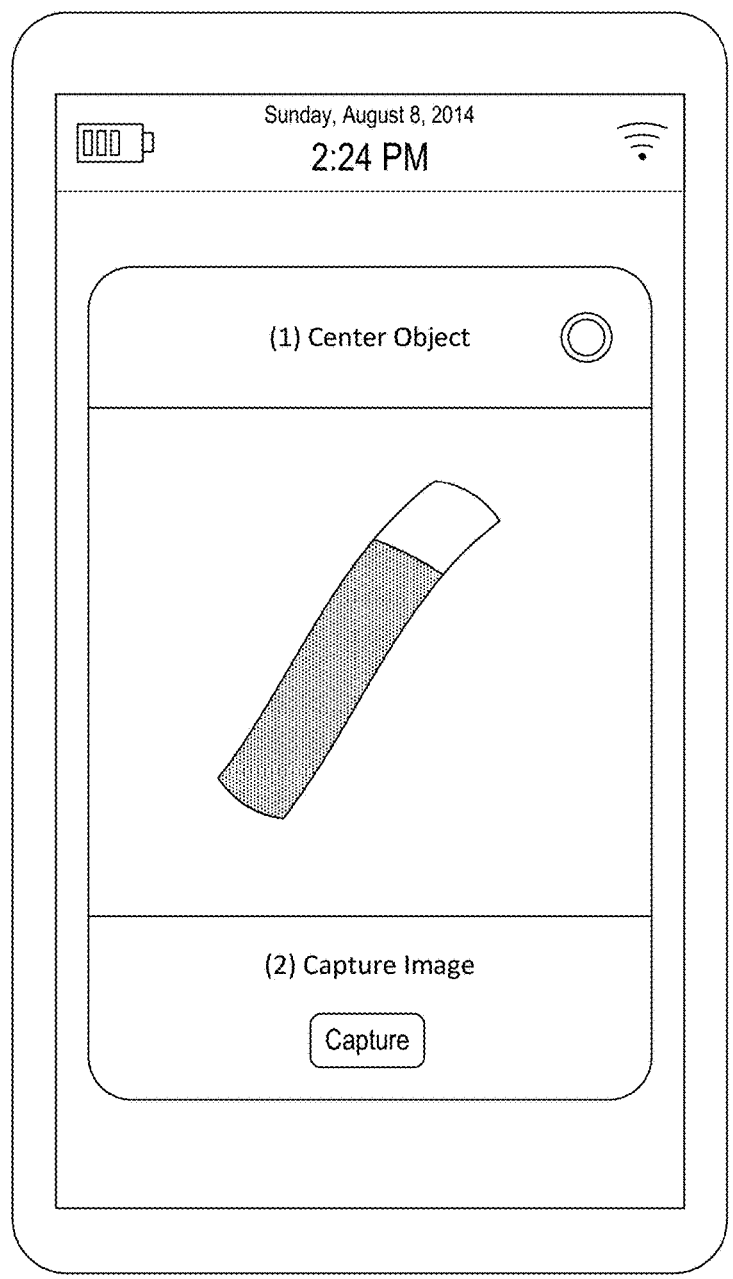
FIG. 1 illustrates an exemplary interface of a software application loaded on a mobile device.

As a preliminary matter, it will readily be understood by one having ordinary skill in the relevant art ("Ordinary Artisan") that the present invention has broad utility and application. As should be understood, any embodiment may incorporate only one or a plurality of the above-disclosed aspects of the invention and may further incorporate only one or a plurality of the above-disclosed features. Furthermore, any embodiment discussed and identified as being "preferred" is considered to be part of a best mode contemplated for carrying out the present invention. Other embodiments also may be discussed for additional illustrative purposes in providing a full and enabling disclosure of the present invention. As should be understood, any embodiment may incorporate only one or a plurality of the above-disclosed aspects of the invention and may further incorporate only one or a plurality of the above-disclosed features. Moreover, many embodiments, such as adaptations, variations, modifications, and equivalent arrangements, will be implicitly disclosed by the embodiments described herein and fall within the scope of the present invention.

Accordingly, while the present invention is described herein in detail in relation to one or more embodiments, it is to be understood that this disclosure is illustrative and exemplary of the present invention, and is made merely for the purposes of providing a full and enabling disclosure of the present invention. The detailed disclosure herein of one or more embodiments is not intended, nor is to be construed, to limit the scope of patent protection afforded the present invention in any claim of a patent issuing here from, which scope is to be defined by the claims and the equivalents thereof. It is not intended that the scope of patent protection afforded the present invention be defined by reading into any claim a limitation found herein that does not explicitly appear in the claim itself.

Thus, for example, any sequence(s) and/or temporal order of steps of various processes or methods that are described herein are illustrative and not restrictive. Accordingly, it should be understood that, although steps of various processes or methods may be shown and described as being in a sequence or temporal order, the steps of any such processes or methods are not limited to being carried out in any particular sequence or order, absent an indication otherwise. Indeed, the steps in such processes or methods generally may be carried out in various different sequences and orders while still falling within the scope of the present invention. Accordingly, it is intended that the scope of patent protection afforded the present invention is to be defined by the issued claim(s) rather than the description set forth herein.

Additionally, it is important to note that each term used herein refers to that which the Ordinary Artisan would understand such term to mean based on the contextual use of such term herein. To the extent that the meaning of a term used herein—as understood by the Ordinary Artisan based on the contextual use of such term—differs in any way from any particular dictionary definition of such term, it is intended that the meaning of the term as understood by the Ordinary Artisan should prevail.

Regarding applicability of 35 U.S.C. §112, ¶6, no claim element is intended to be read in accordance with this statutory provision unless the explicit phrase "means for" or "step for" is actually used in such claim element, whereupon this statutory provision is intended to apply in the interpretation of such claim element.

Furthermore, it is important to note that, as used herein, "a" and "an" each generally denotes "at least one," but does not exclude a plurality unless the contextual use dictates otherwise. Thus, reference to "a picnic basket having an apple" describes "a picnic basket having at least one apple" as well as "a picnic basket having apples." In contrast, reference to "a picnic basket having a single apple" describes "a picnic basket having only one apple."

When used herein to join a list of items, "or" denotes "at least one of the items," but does not exclude a plurality of items of the list. Thus, reference to "a picnic basket having cheese or crackers" describes "a picnic basket having cheese without crackers", "a picnic basket having crackers without cheese", and "a picnic basket having both cheese and crackers." Finally, when used herein to join a list of items, "and" denotes "all of the items of the list." Thus, reference to "a picnic basket having cheese and crackers" describes "a picnic basket having cheese, wherein the picnic basket further has crackers," as well as describes "a picnic basket having crackers, wherein the picnic basket further has cheese."

Referring now to the drawings, one or more preferred embodiments of the present invention are next described. The following description of one or more preferred embodiments is merely exemplary in nature and is in no way intended to limit the invention, its implementations, or uses.

As noted hereinabove, in a healthcare context, an inability to identify or discriminate colors could potentially compromise patient safety, but only a small portion of practicing healthcare providers have been tested for color deficiencies, and many individuals are unaware of their deficiency.

In accordance with one or more preferred implementations, a software application loaded on a mobile device is configured to facilitate color identification. Preferably, the application is configured to effect processing of images captured via a camera of a mobile device for color analysis.

Figure 2:
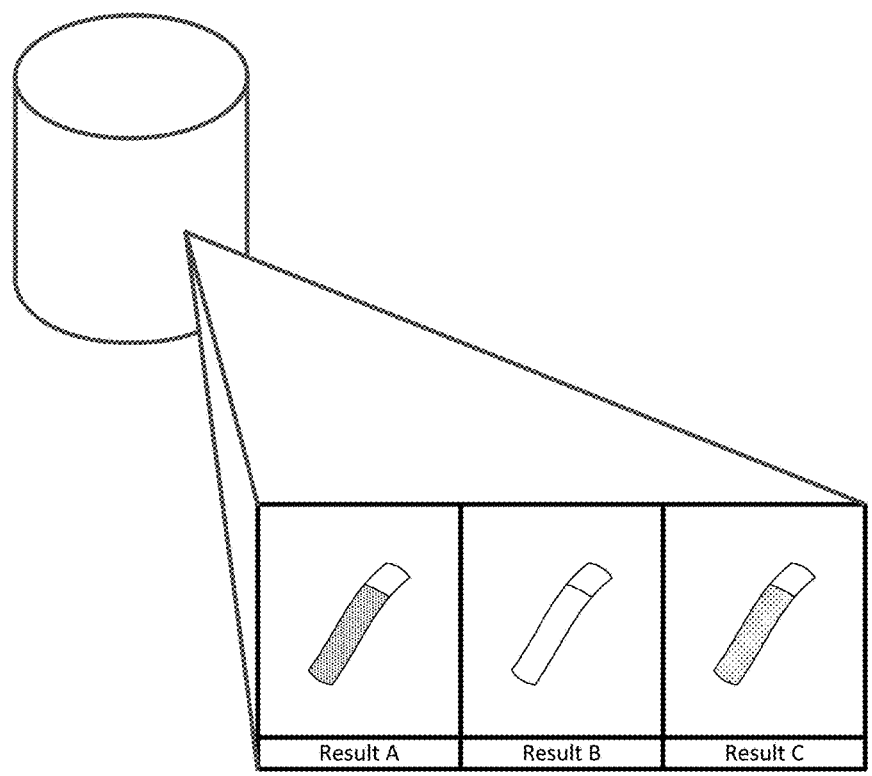
FIG. 2 illustrates a database containing images corresponding to test results for a test strip.

FIG. 1 illustrates an exemplary interface of such a software application loaded on a mobile device. The application allows a user to take a picture of an object using the camera of the mobile device. Thereafter, the captured image is processed, e.g. by programmatically analyzing one or more colors in the captured image corresponding to the object utilizing a database associated with that type of object. An exemplary implementation might compare a captured image of a test strip to one or more images contained in a database corresponding to test results for that type of test strip. FIG. 2 illustrates a database containing such images. In one or more preferred implementations, color processing would be undertaken to compare a color of pixels of a captured image to colors of pixels of stored images.

As another example, a system might compare a captured image of a patient's skin to a database of images of patients having various conditions, such as jaundice. In one or more preferred implementations, analysis might be undertaken of an image of, for example, a patient's skin, throat, eye, ulcer, urine sample, or test strip. In one or more preferred implementations, a user may be asked to, or may be able to, indicate a body part or object that an image is to be captured for, and image comparisons might be limited to stored images associated with that body part or object.

In one or more preferred implementations, image processing might be carried out locally at a mobile device and a database for use in processing may also be stored locally. In one or more preferred implementations, however, the database may be located remotely and/or processing may occur remotely.

Figure 3:
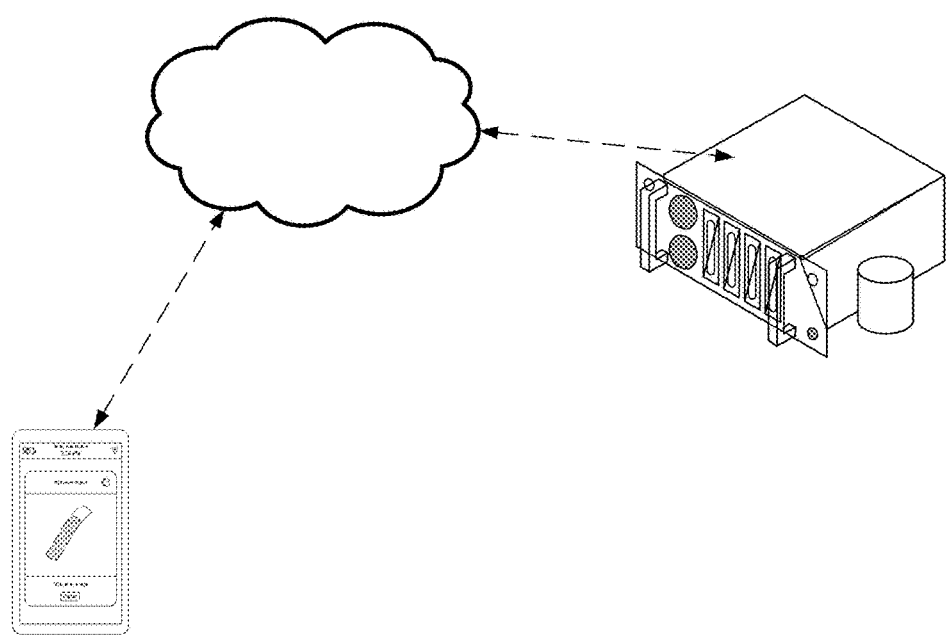
FIG. 3 illustrates a system in which a mobile device accesses a remote database which includes images for comparison.
Figure 4:
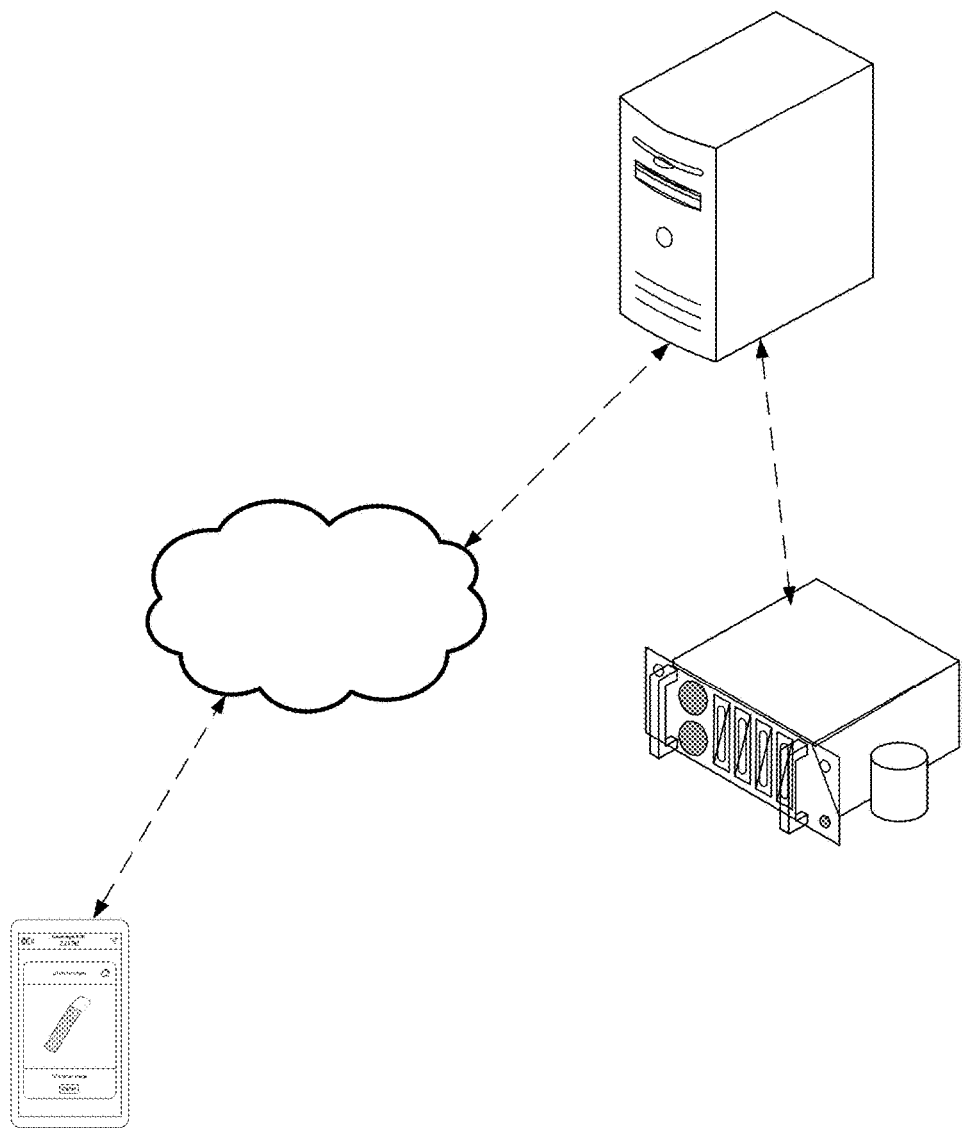
FIG. 4 illustrates a system in which a remote server carries out image processing.

For example, FIG. 3 illustrates a system in which a mobile device accesses a remote database which includes images for comparison, and FIG. 4 illustrates a system in which a remote server carries out image processing. In one or more preferred implementations, results would then be returned to a mobile device. In one or more preferred implementations, results may be sent from a mobile device or remote server to an EHR application or datastore.

In one or more preferred implementations, a software application is configured to account for the lighting conditions an image is taken in.

Based on the foregoing description, it will be readily understood by those persons skilled in the art that the present invention is susceptible of broad utility and application. Many embodiments and adaptations of the present invention other than those specifically described herein, as well as many variations, modifications, and equivalent arrangements, will be apparent from or reasonably suggested by the present invention and the foregoing descriptions thereof, without departing from the substance or scope of the present invention. Accordingly, while the present invention has been described herein in detail in relation to one or more preferred embodiments, it is to be understood that this disclosure is only illustrative and exemplary of the present invention and is made merely for the purpose of providing a full and enabling disclosure of the invention. The foregoing disclosure is not intended to be construed to limit the present invention or otherwise exclude any such other embodiments, adaptations, variations, modifications or equivalent arrangements, the present invention being limited only by the claims appended hereto and the equivalents thereof.

What is claimed is:

1. A method for assisting a health care practitioner in color evaluation, the method comprising:
   (a) maintaining, in a database, a plurality of images each corresponding to a particular result for a healthcare test utilizing a first type of test object;
   (b) capturing, by a healthcare practitioner using a camera of a mobile electronic device, a subject image of a first test object associated with the patient, the first test object being the first type of test object;
   (c) communicating, from the mobile electronic device to a remote server, the captured image of the test object of the first type;
   (d) automatically comparing, at the remote server utilizing one or more electronic processors, the captured subject image to the images maintained in the database for a healthcare test utilizing the first type of test object, such comparison including comparing one or more colors in the subject image to one or more colors in the images maintained in the database;
   (e) automatically determining, at the remote server based on the automatic comparison, that the captured subject image is positively matched to one of the plurality of images maintained in the database;
   (f) communicating, from the remote server to the mobile electronic device, data based on the determination; and
   (g) displaying, to the healthcare practitioner via a display of the mobile electronic device, an indication of the particular result corresponding to the positively matched images.

2. The method of claim 1, wherein the mobile electronic device comprises a phone.

3. The method of claim 1, wherein the mobile electronic device comprises a touchscreen.

4. The method of claim 1, wherein the mobile electronic device comprises a tablet.

5. The method of claim 1, wherein the database comprises a remote database.

6. The method of claim 1, wherein the comparison takes into account a lighting condition of the captured subject image.

7. The method of claim 1, wherein the first type of test object is a test strip.

8. The method of claim 1, wherein the first type of test object is a urine sample.

9. A method for assisting a health care practitioner in color evaluation, the method comprising:
   (a) maintaining, in a database, a plurality of images of test objects of various types, each image corresponding to a particular result;
   (b) capturing, by a healthcare practitioner using a camera of a mobile electronic device, a subject image of a first test object associated with the patient, the first test object being a first type of test object of the various types of test objects;
   (c) communicating, from the mobile electronic device to a remote server, the captured image of the first test object;
   (e) determining a subset of the maintained plurality of images which correspond to the first type of test object;
   (d) automatically comparing, at the remote server utilizing one or more electronic processors, the captured subject image to the determined subset of images maintained in the database for a healthcare test utilizing the first type of test object, such comparison including comparing one or more colors in the subject image to one or more colors in the determined subset of images maintained in the database;

(e) automatically determining, based on the automatic comparison, that the captured subject image is positively matched to one of the plurality of images maintained in the database;

(f) communicating, from the remote server to the mobile electronic device, data based on the determination; and (g) displaying, to the healthcare practitioner via a display of the mobile electronic device, an indication of the particular result corresponding to the positively matched image.

10. The method of claim 9, wherein the mobile electronic device comprises a phone.

11. The method of claim 9, wherein the mobile electronic device comprises a touchscreen.

12. The method of claim 9, wherein the mobile electronic device comprises a tablet.

13. The method of claim 9, wherein the database comprises a remote database.

14. The method of claim 9, wherein the comparison takes into account a lighting condition of the captured subject image.

15. The method of claim 9, wherein the first type of test object is a test strip.

16. The method of claim 9, wherein the first type of test object is a urine sample.

* * * * *